United States Patent
Filipour (10) Patent No.: US 11,351,217 B2
(45) Date of Patent: Jun. 7, 2022

(54) METHOD FOR MANUFACTURING AN ULCER TREATMENT

(71) Applicant: Fatemeh Sohela Filipour, Herndon, VA (US)

(72) Inventor: Fatemeh Sohela Filipour, Herndon, VA (US)

( * ) Notice: Subject to any disclaimer, the term of this patent is extended or adjusted under 35 U.S.C. 154(b) by 163 days.

(21) Appl. No.: 16/935,076

(22) Filed: Jul. 21, 2020

(65) Prior Publication Data

US 2022/0023371 A1 Jan. 27, 2022

(51) Int. Cl.
*A61K 36/49* (2006.01)

(52) U.S. Cl.
CPC .................................. *A61K 36/49* (2013.01)

(58) Field of Classification Search
CPC ....................................................... A61K 36/49
See application file for complete search history.

(56) References Cited

U.S. PATENT DOCUMENTS

| | | |
|---|---|---|
| 2008/0175934 A1 | 7/2008 | Mitra |
| 2012/0329736 A1 | 12/2012 | Huang |
| 2016/0022755 A1* | 1/2016 | Sepahvand ............ A61K 36/49 424/776 |

FOREIGN PATENT DOCUMENTS

WO WO1993019765 A1 10/1993

OTHER PUBLICATIONS

Delfan, Bahram & Bahmani, Mahmoud & Hassanzadazar, Hassan & Saki, Kourosh & Rafieian-kopaei, Mahmoud & Rashidipour, Marzieh & Bagheri, Farid. (2014). Ethnobotany study of effective medicinal plants on gastric problems in Lorestan province, West of Iran. 2015. 483-492.

Ghasemi Pirbalouti, Abdollah & Bahmani, Mahmoud & Avijgan, Majid. (2009). Anti-Candida activity of some of the Iranian medicinal plants. Electronic Journal of Biology. 5. 85-88.

Sadeghian, Issa & Hassanshahian, Mehdi & Sadeghian, Sakine & Jamali, Shole & Antimicrobial, Jamali. (2012). Antimicrobial Effects of Quercus Brantii Fruits on Bacterial Pathogens. Jundishapur Journal of Microbiology. 5. 10.5812/jjm.3376.

* cited by examiner

*Primary Examiner* — Aaron J Kosar (57) ABSTRACT

A method of manufacturing an ulcer treatment is disclosed. Ulcer symptoms, including stomach pain, bloating, heartburn, nausea, and more, can be highly intrusive on a patient's life. In order to create a treatment, several acorns, particularly acorns from *Quercus brantii*, commonly known as a Persian Oak tree, are acquired. These acorns are sorted and subsequently washed in water to free them of any dirt or contaminants. The acorns are then crushed to separate the acorn nuts from their corresponding acorn shells. The shells are discarded, and the acorn nuts are washed in room-temperature water again to remove any nut impurities. The acorn nuts are then roasted in an oven for several minutes to remove the nut skin from the nut. The nut skin and the nut body are collected and pulverized separately to create an ulcer-treating powder. The ulcer-treating powder may subsequently be mixed into a solvent and ingested by the ulcer patient to treat the patient's ulcers and ulcer symptoms.

9 Claims, 9 Drawing Sheets

METHOD FOR MANUFACTURING AN ULCER TREATMENT

FIELD OF THE INVENTION

The present invention generally relates to a method for developing an ulcer treatment. More specifically, the present invention relates to a method of processing Persian Oak acorns to generate a medicinal powder which, when consumed, reduces the symptoms of ulcers.

BACKGROUND OF THE INVENTION

In today's society, more and more people are finding themselves relying on pharmaceutical medication to alleviate themselves of their illnesses and pain. However, many people are finding that reliance on pharmaceuticals to be costly, detrimental to their health, or both. Pharmaceutical medications can be very expensive for users because pharmaceutical companies pour numerous financial resources into researching chemical formulas that can be used for curing illnesses. This has the effect of making pharmaceutical medications higher in cost than non-pharmaceutical medication. Also, pharmaceutical medications are heavily regulated by government agencies, which pharmaceutical companies overcome by increasing the price of their pharmaceutical medications. For example, sucralfate is a pharmaceutical medication that is used for treating stomach ulcers. It can cost anywhere between $30 and $65 for a single 30-day supply. Also, pharmaceutical medications contain a variety of chemicals, which often can have side-effects that can have a detrimental effect on the user's health, despite the benefits for curing stomach ulcers. For instance, sucralfate is known to have side-effects of convulsions, which, if left untreated, can lead to injury and/or death.

To address the issues of taking pharmaceutical medications, society is beginning to reject the use of pharmaceutical medications and are starting to instead use herbal medication. Herbal medication is made of herbs, plant life, and other similar materials. Herbs can refer to any plant-like substance or plant by-product that usually has not been chemically altered. Herbal medications are often cheaper than pharmaceutical medications because herbal medications are not as heavily regulated or researched as pharmaceutical medications. Also, since most herbal medications do not contain chemicals that are often found in pharmaceutical medications, most herbal medications consequently do not share some of the same side-effects that pharmaceutical medications may have. However, herbal medications can be inefficient since most herbal medications are made using nomadic methods and processes based upon ancient knowledge. For instance, there are many papers that discuss the many nomadic treatments that are used to treat illnesses, like the use of crushed acorns in stomach ulcer remedies. These methods do not document which components of the acorn is useful in these remedies, or how best to treat and prepare the acorns for processing. The present invention documents which components of the acorn are useful in the treatment of stomach ulcers, as well as a process for preparing those components for usage as an ulcer treatment.

The present invention is an herbal medication that utilizes acorns from Persian oak trees. Specifically, the present invention utilizes the skin and fruit extracted from the Persian oak acorns and processes them into a powdered compound. The compound can be subsequently dissolved into a solvent, which can then be ingested or consumed by the user. Although there are pharmaceutical medications that are used in treating stomach ulcers, the objective of the present invention is to resolve stomach ulcers in users at a lower cost than those of pharmaceutical medication and utilize naturally-occurring solutions instead of a variety of chemicals. Additionally, the present invention does not contain any added chemicals, like those found in pharmaceutical medications; therefore, the present invention would not have any of the side-effects associated with pharmaceutical medications that do have chemicals within. Although there exist nomadic remedies that do not contain chemicals like the present invention, the present invention differs from current nomadic remedies by using processing technologies that are more effective, efficient, and consistent.

DETAILED DESCRIPTION OF THE INVENTION

All illustrations of the drawings are for the purpose of describing selected versions of the present invention and are not intended to limit the scope of the present invention.

The present invention is a method for manufacturing an ulcer treatment that allows for conversion of acorns into an ulcer treatment. Peptic ulcers, including both gastric ulcers and duodenal ulcers, are painful sore spots in the stomach or the small intestine. These sore spots can result in a wide variety of symptoms, including abdominal discomfort, bloating, heartburn, nausea, and more. The present invention describes a means of processing acorns that results in a powder. This powder, when ingested or otherwise consumed by a user, results in the reduction of incidence of ulcers and the treatment of symptoms.

Figure 1:
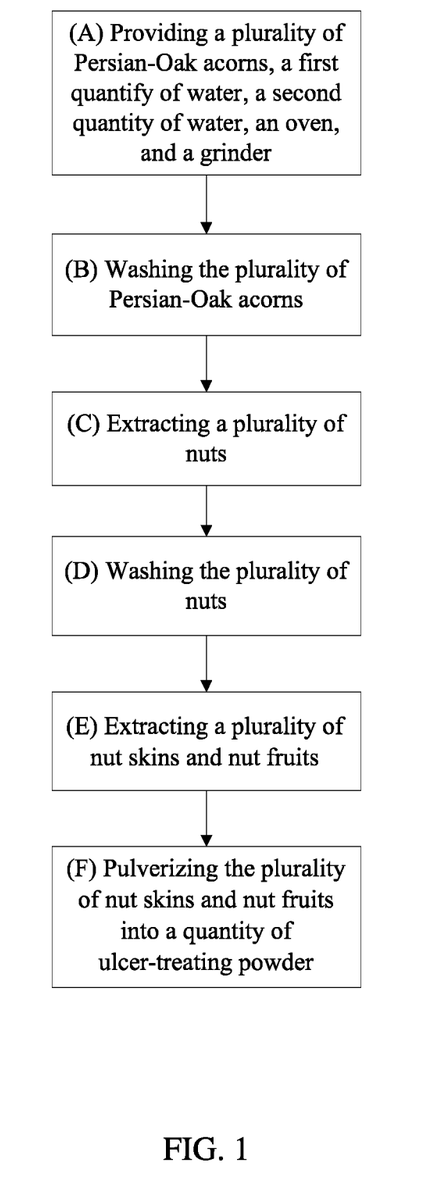
FIG. 1 is a flowchart illustrating the overall process for the present invention.

As can be seen in FIG. 1, the method of the present invention follows an overall process that allows for an effective and efficient conversion of acorns into an ulcer treatment. In order to execute the overall process for the method of the present invention, the present invention requires a plurality of Persian-Oak acorns, a first quantity of water, a second quantity of water, an oven, and a grinder (Step A). In alternative embodiments, it may be possible to provide a plurality of acorns of other varieties; however, the preferred embodiment utilizes the properties of Persian-Oak acorns specifically. The first quantity of water and the second quantity of water, ultimately utilized during various washing phases of the present invention, are both preferably at room temperature. The oven is a thermally-controlled space that allows the user to perform heat treatments upon the plurality of Persian-Oak acorns. The grinder is a mechanical device capable of pulverizing the processed results of the plurality of Persian-Oak acorns into the ulcer treatment powder that is the final product of the present invention.

In accordance with the preferred embodiment of the present invention, the plurality of Persian-Oak acorns is washed in the first quantity of water (Step B). This step removes dirt, dust, grime, and other contaminants from the plurality of Persian-Oak acorns. A plurality of nuts is then extracted from the plurality of Persian-Oak acorns (Step C). The shells are removed from each of the plurality of Persian-Oak acorns to expose and retrieve the plurality of nuts. Next, the plurality of nuts is washed in the second quantity of water (Step D). This ensures that there are no contaminants remaining on the plurality of nuts, particularly on the exterior of the plurality of nuts. A plurality of nut skins is then extracted from the plurality of nuts by roasting the plurality of nuts within the oven (Step E). This process dries the plurality of nuts until the plurality of nut skins easily separates from the plurality of nuts. Finally, the grinder the plurality of nut skins and nut fruits is pulverized into a quantity of ulcer-treating powder (Step F). The grinder allows the user to grind, crush, churn, pound, pulverize, or otherwise process the roasted plurality of nut skins and nut fruits into the desired powder form.

Figure 2:
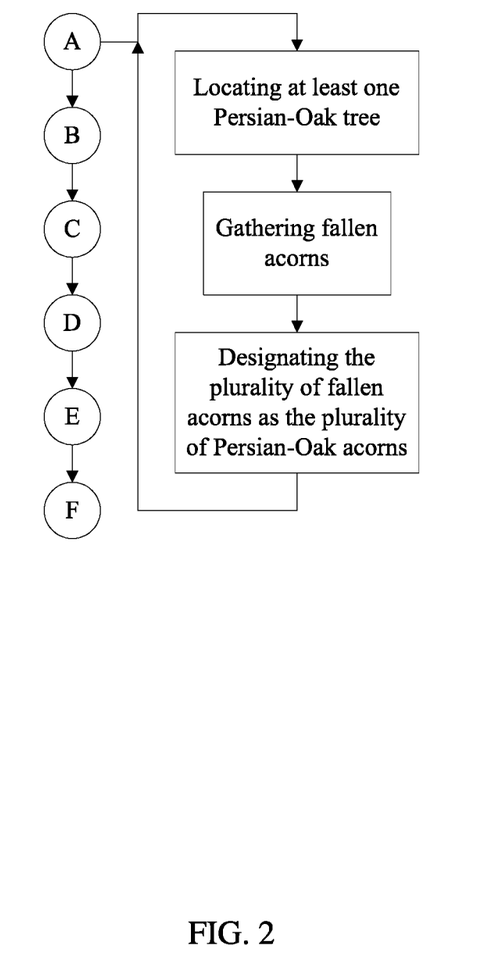
FIG. 2 is a flowchart illustrating the process of gathering a plurality of Persian-Oak acorns.

While the plurality of Persian-Oak acorns may be gathered in a variety of ways, in the preferred embodiment of the present invention, the plurality of Persian-Oak acorns is gathered from Persian-Oak trees during Step A, which is shown in FIG. 2. The gatherer locates at least one Persian-Oak Tree. The gatherer then collects a plurality of fallen acorns surrounding the at least one Persian-Oak tree. This ensures that the user is acquiring mature acorns with fully-formed nuts, whereas pulling acorns from the at least one Persian-Oak tree may result in less-than fully-formed nuts. In an exemplary embodiment, the collected acorns are then evaluated, and acorns deemed too damaged, young, or otherwise faulty, are discarded. The collected acorns are then designated as the plurality of Persian-Oak acorns that will be used in the subsequent processing for the present invention.

Figure 3:
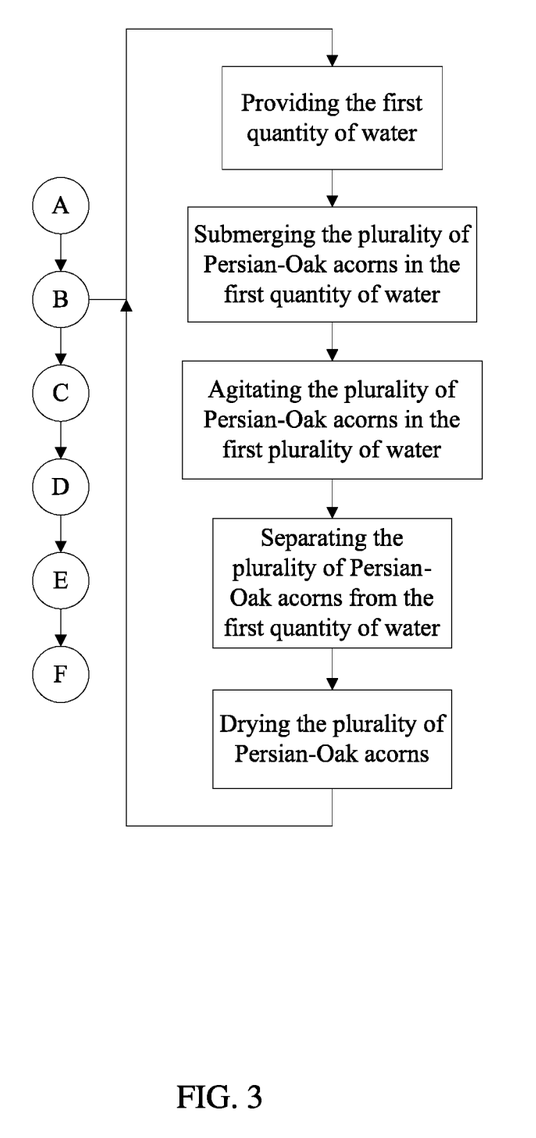
FIG. 3 is a flowchart illustrating the process of washing the plurality of Persian-Oak acorns.

As can be seen in FIG. 3, Step B begins by providing the first quantity of water, preferably at room temperature. The plurality of Persian-Oak acorns is submerged within the first quantity of water. This ensures full coverage of the plurality of Persian-Oak acorns, so that no dirt or contaminants remain isolated from the first quantity of water. The plurality of Persian-Oak acorns is then agitated within the first quantity of water in order to dislodge and remove dirt and other contaminants. The first quantity of water is then removed from the plurality of Persian-Oak acorns. This may be accomplished through the use of a strainer or other filtering means. Next, the plurality of Persian-Oak acorns is dried. The drying occurs by arranging the plurality of Persian-Oak acorns offset from each other across a flat surface, thus providing each of the plurality of Persian-Oak acorns with space to allow evaporation to occur.

Figure 4:
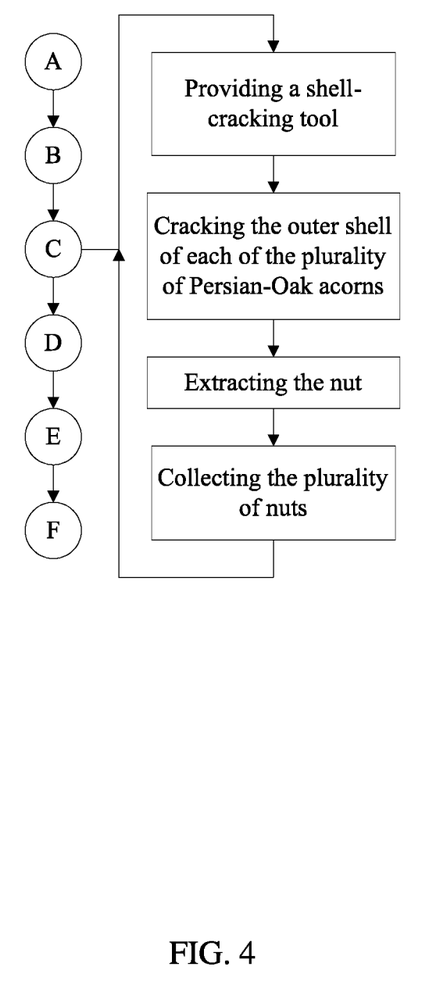
FIG. 4 is a flowchart illustrating the process of extracting a plurality of nuts.

Following Step B, Step C begins by providing a shell-cracking tool, which is shown in FIG. 4. The shell-cracking tool may be any of a variety of devices capable of opening the plurality of Persian-Oak acorns without damaging the plurality of nuts within. A blunt object like a hammer or hydraulic press could crack the plurality of nuts effectively; a large-intake nut cracker could also be effective. The outer shell of each acorn of the plurality of Persian-Oak acorns is cracked by actuating the shell-cracking tool. A desired nut is then extracted from each of the plurality of Persian-Oak acorns by discarding the outer shell of each of the plurality of Persian-Oak acorns. The remaining plurality of nuts is then collected for subsequent use.

Figure 5:
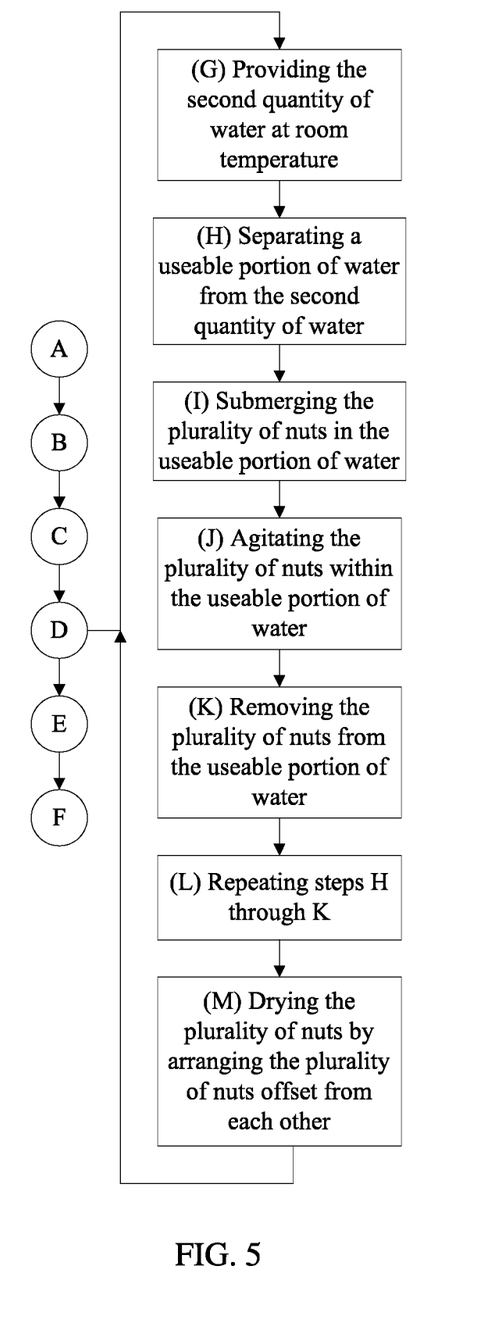
FIG. 5 is a flowchart illustrating the process of washing the plurality of nuts.

After Step C concludes, Step D begins by providing the second quantity of water at room temperature (Step G), which is shown in FIG. 5. A useable portion of water is separated from the second quantity of water (Step H). This useable portion of water is subsequently utilized for the second washing step. The plurality of nuts is submerged within the useable portion of water (Step I). This ensures full coverage of the plurality of nuts, so that no dirt or contaminants remain isolated from the plurality of nuts. The plurality of nuts is subsequently agitated within the useable portion of water in order to dislodge and remove remaining dirt and other contaminants (Step J). The useable portion of water is then removed from the plurality of nuts (Step K). This may be accomplished through the use of a strainer or other filtering means. A plurality of necessary iterations for Steps H through K, wherein each necessary iteration separates a new usable portion of water from the second quantity of water, is then performed (Step L). This ensures that the exterior for each of the plurality of nuts is at optimal cleanliness. Finally, the plurality of nuts is dried by arranging the plurality of nuts offset from each other across a flat surface, thus providing each of the plurality of nuts with space to allow evaporation to occur (Step M).

Figure 6:
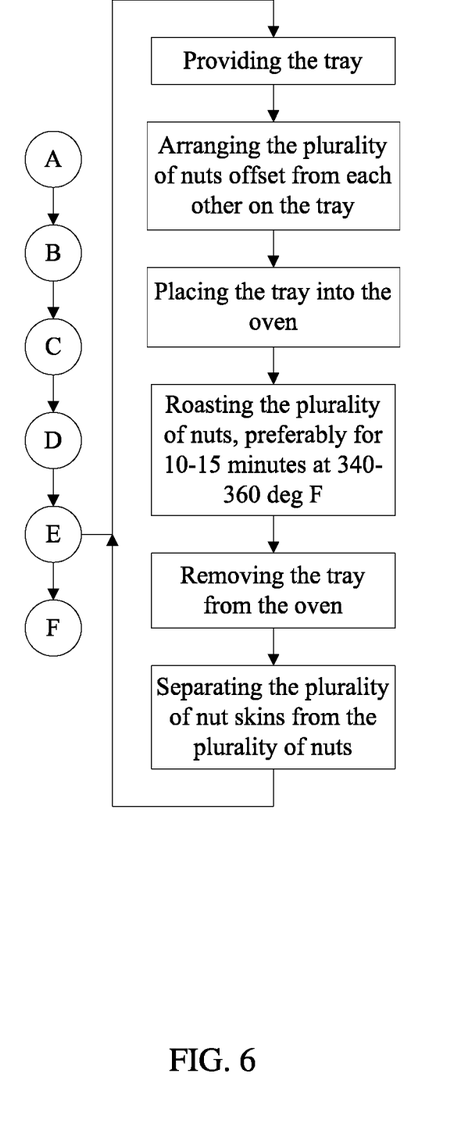
FIG. 6 is a flowchart illustrating the process of extracting a plurality of nut skins.
Figure 7:
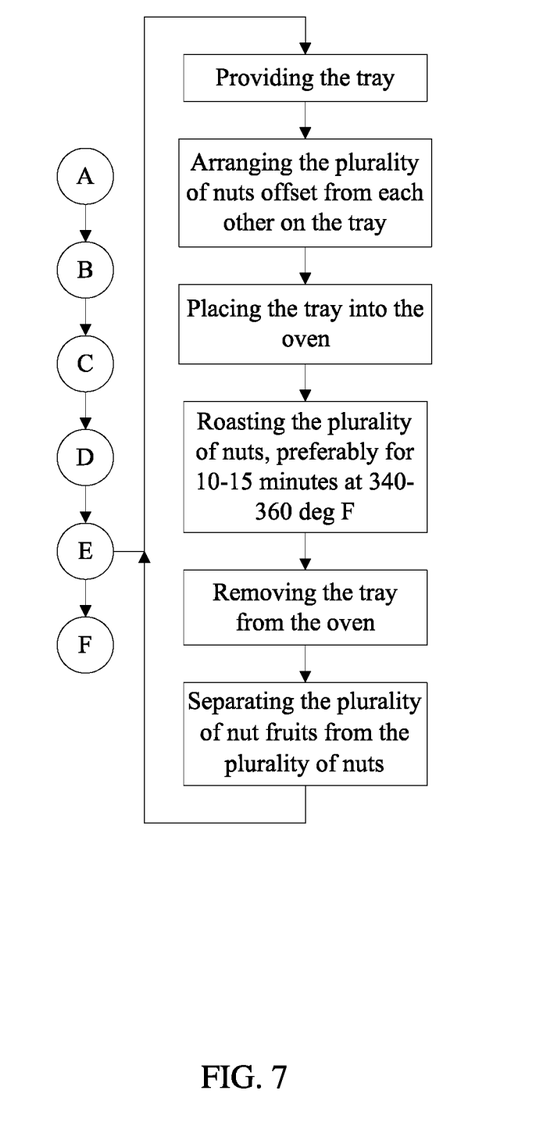
FIG. 7 is a flowchart illustrating the process of extracting a plurality of nut fruits.

Upon completion of the drying phase of Step D, Step E begins by providing a tray, which is shown in FIGS. 6 and 7. The plurality of nuts is arranged offset from each other across the tray. Arranging the plurality of nuts in this manner ensures even application of heat. The tray is then placed into the oven. The plurality of nuts is roasted within the oven for a specified amount of time at a specified temperature, or until peeling of the outer skin of each nut of the plurality of nuts is observed. The temperature range for the oven is between 340 and 360 degrees Fahrenheit. This ensures adequate roasting of the plurality of nuts, so that the plurality of nuts is adequately heated, but the plurality of nut skins does not become damaged. The designated period for cooking the plurality of nuts is 10-15 minutes. This ensures adequate roasting of the plurality of nuts, so that the plurality of nuts is adequately heated, but the plurality of nut skins does not become damaged. Upon roasting completion, the tray is removed from the oven in order to cool the plurality of nuts and the plurality of nut skins. The plurality of nut skins is then separated from the plurality of nuts. In an exemplary embodiment, the plurality of nuts is then discarded, leaving the plurality of nut skins to be utilized in subsequent processing of the present invention.

Figure 8:
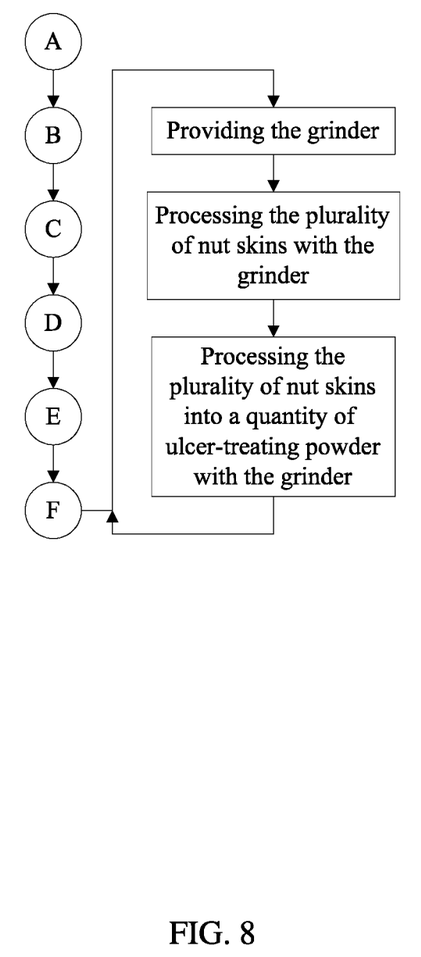
FIG. 8 is a flowchart illustrating the process of pulverizing the plurality of nut skins into a quantity of ulcer-treating powder.
Figure 9:
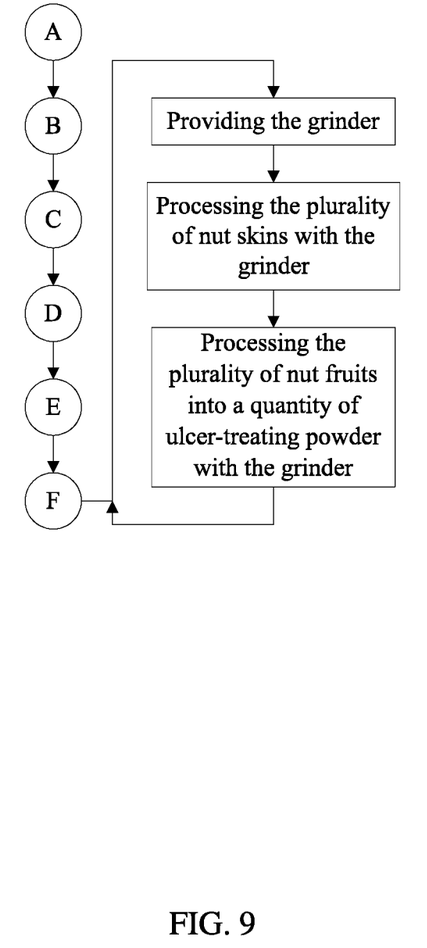
FIG. 9 is a flowchart illustrating the process of pulverizing the plurality of nut fruits into a quantity of ulcer-treating powder.

Upon completion of Step E, Step F begins by providing the grinder, which is shown in FIGS. 8 and 9. The plurality of nut skins is crushed, grated, ground, pulverized, or otherwise processed by the grinder in order to reduce solid content to a quantity of ulcer-treating powder. In an exemplary embodiment, the plurality of nut skins is processed until the quantity of ulcer-treating powder is a coarse texture.

In an exemplary embodiment, upon completion of separation of the plurality of nuts from the plurality of nut skins in Step E, both the plurality of nuts and the plurality of nut skins are retained for further processing. Next, in Step F, the plurality of nut skins is crushed, grated, ground, pulverized, or otherwise processed by the grinder in order to reduce solid content to a quantity of nut skin powder. Furthermore, the plurality of nuts is also crushed, grated, ground, pulverized, or otherwise processed by the grinder in order to reduce solid content to a quantity of nut powder. The resultant quantity of nut skin powder and quantity of nut powder are then combined into a quantity of ulcer-treating powder. In an exemplary embodiment, the quantity of nut skin powder and quantity of nut powder are combined in a 1:2 ratio, preferably by weight. This arrangement ensures both efficient utilization of resources and highly effective ulcer treatment properties of the resultant mixture.

In an exemplary embodiment of Step A, the acorn acquisition step further comprises a quality control step. The quality control step is a way to generate high quality ulcer treatment yield by ensuring the source material is high quality. The quality control step takes place after gathering of the plurality of Persian-Oak acorns. The plurality of Persian-Oak acorns is inspected for shape inconsistencies, weight, color, and other such metrics. Healthy acorns are separated from unhealthy acorns. The unhealthy acorns are discarded. Then, Step A continues with designating the plurality of sorted acorns as the plurality of Persian-Oak acorns.

In order to properly utilize the quantity of ulcer-treating powder, the quantity of ulcer-treating powder is ingested by the user. The quantity of ulcer-treating powder is mixed into a solvent. The quantity of ulcer-treating powder within the solvent is then swallowed by the user, thus allowing the quantity of ulcer-treating powder to contact the affected stomach area. The user can remove an amount of ulcer-treating powder from a container and dissolve that dosage into a solvent before consuming the mixture/compound. The preferred solvent is a yogurt, or a puree; however, any solvent is applicable for the present invention, including water, juices, and other fluids. The amount of ulcer-treating powder for curing the user of their stomach ulcers is approximately one tablespoon; however, any amount/dosage of the present invention can be safely consumed.

The exact compositional breakdown of the compound is as follows: 40-60% carbohydrates, 30-40% water, 3-5% protein, 3-5% fiber, 1-2% ash, and 3-5% fat. The fat content is further broken down into the following: 5-15% omega-3 fatty acid and 85-95% omega-6 and omega-9 fatty acids. These contents are all naturally derived from the skin and the nut fruit from Persian-Oak acorns.

Although the invention has been explained in relation to its preferred embodiment, it is to be understood that many other possible modifications and variations can be made without departing from the spirit and scope of the invention as hereinafter claimed.

What is claimed is:

1. A method for manufacturing an ulcer treatment, the method comprising the steps of:
   (A) providing a plurality of Persian oak acorns, a first quantity of water, a second quantity of water, an oven, and a grinder;
   (B) washing the plurality of Persian oak acorns in the first quantity of water;
   (C) extracting a plurality of nuts by removing an outer shell from each of the plurality of Persian oak acorns;
   (D) washing the plurality of nuts in the second quantity of water;
   (E) extracting a plurality of nut skins and nut fruit by roasting the plurality of nuts within the oven; and
   (F) pulverizing the plurality of nut skins and nut fruit into a quantity of ulcer-treating powder with the grinder.

2. The method for manufacturing an ulcer treatment, the method as claimed in claim 1 comprising the steps of:
   locating at least one Persian oak;
   gathering a plurality of fallen acorns surrounding the at least one Persian oak; and
   designating the plurality of fallen acorns as the plurality of Persian oak acorns.

3. The method for manufacturing an ulcer treatment, the method as claimed in claim 1 comprising the steps of:
   providing the first quantity of water at room temperature;
   submerging the plurality of Persian oak acorns within the first quantity of water;
   agitating the plurality of Persian oak acorns within the first quantity of water;
   separating the plurality of Persian oak acorns from the first quantity of water; and
   drying the plurality of Persian oak acorns by arranging the plurality of Persian-Oak acorns offset from each other across a flat surface.

4. The method for manufacturing an ulcer treatment, the method as claimed in claim 1 comprising the steps of:
   providing a shell-cracking tool;
   cracking the outer shell of each of the plurality of Persian oak acorns by actuating the shell-cracking tool; and
   extracting a desired nut from each of the plurality of Persian oak acorns by discarding the outer shell of each of the plurality of Persian oak acorns.

5. The method for manufacturing an ulcer treatment, the method as claimed in claim 1 comprising the steps of:
   (G) providing the second quantity of water at room temperature;
   (H) separating a usable portion of water from the second quantity of water;
   (I) submerging the plurality of nuts within the usable portion of water;
   (J) agitating the plurality of nuts within the usable portion of water;
   (K) separating the plurality of nuts from the usable portion of water;
   (L) executing a plurality of necessary iterations for steps (H) through (K), wherein each necessary iteration separates a new usable portion of water from the second quantity of water; and
   (M) drying the plurality of nuts by arranging the plurality of nuts offset from each other across a flat surface.

6. The method for manufacturing an ulcer treatment, the method as claimed in claim 1 comprising the steps of:
   providing a tray;
   arranging the plurality of nuts offset from each other across the tray;
   placing the tray with the plurality of nuts in the oven;
   peeling the plurality of nut skins off the plurality of nuts by heating the plurality of nuts at a specified temperature range for a designated period of time;
   removing the tray from the oven in order to cool the plurality of nuts and the plurality of nut skins; and
   separating the plurality of nut skins from the plurality of nuts.

7. The method for manufacturing an ulcer treatment, the method as claimed in claim 6, wherein the specified temperature range is between 340 and 360 degrees Fahrenheit.

8. The method for manufacturing an ulcer treatment, the method as claimed in claim 6, wherein the designated period of time ranges between 10 to 15 minutes.

9. The method for manufacturing an ulcer treatment, the method as claimed in claim 1, wherein the quantity of ulcer-treating powder is a coarse texture.

* * * * *